(12) United States Patent
Ogawa et al.

(10) Patent No.: US 12,715,833 B2
(45) Date of Patent: Aug. 25, 2026

(54) METHOD FOR PRODUCING (METH)ACROLEIN AND METHOD FOR PRODUCING (METH)ACRYLIC ACID

(71) Applicant: Mitsubishi Chemical Corporation, Tokyo (JP)

(72) Inventors: Yasushi Ogawa, Tokyo (JP); Yoshimune Abe, Tokyo (JP); Takuya Nakamura, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 911 days.

(21) Appl. No.: 17/805,074

(22) Filed: Jun. 2, 2022

(65) Prior Publication Data

US 2022/0289658 A1 Sep. 15, 2022

Related U.S. Application Data

(63) Continuation of application No. PCT/JP2021/002603, filed on Jan. 26, 2021.

(30) Foreign Application Priority Data

Feb. 5, 2020 (JP) ................................ 2020-017679

(51) Int. Cl.
*B01J 23/28* (2006.01)
*B01J 8/06* (2006.01)
(Continued)

(52) U.S. Cl.
CPC ............ *C07C 51/252* (2013.01); *B01J 8/065* (2013.01); *B01J 8/067* (2013.01); *B01J 23/28* (2013.01);
(Continued)

(58) Field of Classification Search
CPC ........ C07C 51/252; C07C 45/34; B01J 8/065; B01J 8/067; B01J 23/28; B01J 2208/065
See application file for complete search history.

(56) References Cited

U.S. PATENT DOCUMENTS 4,873,368 A 10/1989 Kadowaki et al.
6,069,271 A 5/2000 Tanimoto et al.
(Continued)

FOREIGN PATENT DOCUMENTS

CN 1599708 A 3/2005
EP 0 911 313 B1 9/2001
(Continued)

OTHER PUBLICATIONS

Concise Enc. Adv. Ceram. Mater. 1991, pp. 248-252 (Smoke) (Year: 1991).*
(Continued)

*Primary Examiner* — Amy C Bonaparte
*Assistant Examiner* — Derek Rhoades
(74) *Attorney, Agent, or Firm* — Oblon, McClelland, Maier & Neustadt, L.L.P.

(57) ABSTRACT

A method for producing (meth)acrolein by vapor-phase catalytic oxidation of propylene or isobutylene in a multi-tubular reactor including a plurality of reaction tubes, the reaction tubes each including a reaction zone filled with a catalyst including molybdenum oxide and a cooling zone filled with an inert substance, wherein a temperature of a heat medium that flows outside the cooling zone is lower than a temperature of a heat medium that flows outside the reaction zone, and wherein the inert substance includes an inert substance having a major-axis length that is equal to or more than 1.7 times a major-axis length of the catalyst. A method for producing (meth)acrylic acid in which (meth)
(Continued)

acrolein thus produced is converted to (meth)acrylic acid by vapor-phase catalytic oxidation.

20 Claims, 4 Drawing Sheets

(51) Int. Cl.

| | |
|---|---|
| ***B01J 35/40*** | (2024.01) |
| ***B01J 35/55*** | (2024.01) |
| ***C07C 45/34*** | (2006.01) |
| ***C07C 51/25*** | (2006.01) |

(52) U.S. Cl.

CPC ............... *B01J 35/40* (2024.01); *B01J 35/55* (2024.01); *C07C 45/34* (2013.01); *B01J 2208/065* (2013.01)

(56) References Cited

U.S. PATENT DOCUMENTS

| | | | |
|---|---|---|---|
| 7,544,836 B2 | 6/2009 | Jinno et al. | |
| 7,563,927 B2 | 7/2009 | Ogawa et al. | |
| 2004/0249000 A1 | 12/2004 | Yada et al. | |
| 2007/0021631 A1 | 1/2007 | Yada et al. | |
| 2007/0021632 A1 | 1/2007 | Yada et al. | |
| 2008/0045748 A1 | 2/2008 | Jinno et al. | |
| 2011/0178334 A1 | 7/2011 | Tanimoto et al. | |
| 2015/0274629 A1 * | 10/2015 | Schliephake et al. | C07C 51/25 |

FOREIGN PATENT DOCUMENTS

| | | | |
|---|---|---|---|
| IN | 2006DELNP06035 A1 | 4/2007 | |
| JP | 56-73041 A | 6/1981 | |
| JP | 4-279542 A | 10/1992 | |
| JP | 11-130722 A | 5/1999 | |
| JP | 0911313 B1 * | 9/2001 | C07C 51/25 |
| JP | 2005-325043 A | 11/2005 | |
| JP | 2010-77088 A | 4/2010 | |
| JP | 2010-529005 A | 8/2010 | |
| RU | 2 309 794 C2 | 11/2007 | |
| RU | 2 309 936 C2 | 11/2007 | |
| RU | 2 346 735 C2 | 2/2009 | |
| RU | 2 346 929 C2 | 2/2009 | |
| WO | WO 2010/032665 A1 | 3/2010 | |

OTHER PUBLICATIONS

Russian Office Action and Search Report issued Apr. 9, 2024 in corresponding Russian Patent Application No. 2022123453 (with English machine translation), 11 pages.

International Search Report issued Apr. 13, 2021 in PCT/JP2021/002603, filed Jan. 26, 2021, 2 pages.

Fulton, J. "Regenerating spent catalyst" CE Refresher Catalyst Engineering 8. (1988) (4 pages).

Extended European Search Report issued on Jul. 6, 2023 in European Patent Application No. 21750146.9, 7 pages.

Japanese Office Action issued on Sep. 10, 2024 in Japanese Patent Application No. 2021-010407 (with unedited, machine-generated English translation, 8 pages.

Combined Chinese Office Action and Search Report issued Aug. 30, 2023 in Chinese Patent Application No. 202180006945.2 (with English Translation of Office Action Only), 8 pages.

Indian Office Action issued Mar. 18, 2025 in Indian Patent Application No. 202247048147, 6 pages.

* cited by examiner

METHOD FOR PRODUCING (METH)ACROLEIN AND METHOD FOR PRODUCING (METH)ACRYLIC ACID

CROSS-REFERENCE TO RELATED APPLICATIONS

The present application is a bypass continuation of international application PCT/JP2021/002603, filed on Jan. 26, 2021, and claims the benefit of the filing date of Japanese Appl. No. 2020-017679, filed on Feb. 5, 2020, the content of each of which is incorporated by reference.

TECHNICAL FIELD

The present invention relates to a method for producing (meth)acrolein by vapor-phase catalytic oxidation using a multitubular reactor that includes a plurality of reaction tubes each including a reaction zone and a cooling zone. The present invention relates also to a method for producing (meth)acrylic acid by the vapor-phase catalytic oxidation of (meth)acrolein produced by the method for producing (meth) acrolein.

The term "(meth)acrolein" used herein refers to "acrolein and/or methacrolein". The term "(meth)acrylic acid" used herein refers to "acrylic acid and/or methacrylic acid".

BACKGROUND ART

One of the methods for producing (meth)acrolein and (meth)acrylic acid is a method in which the vapor-phase catalytic oxidation of propylene or isobutylene is performed using an oxygen-containing gas in the presence of a catalyst to produce (meth)acrolein and the vapor-phase catalytic oxidation of the (meth)acrolein is further performed to produce a reaction gas containing (meth)acrylic acid.

In such a facility for commercial manufacturing (meth) acrolein or (meth)acrylic acid by vapor-phase catalytic oxidation, a multitubular reactor that includes a plurality of reaction tubes each including a reaction zone and a cooling zone is commonly used. A multitubular reactor is advantageous in that, for example, the temperature of each reaction tube can be maintained to be equal to or higher than the temperature required for vapor-phase catalytic oxidation; a large amount of heat produced by oxidation can be removed; and a plug flow can be formed in each reaction tube and, consequently, a high reaction conversion ratio can be achieved.

(Meth)acrolein produced by vapor-phase catalytic oxidation reacts with oxygen included in the gas phase to cause oxidation (hereinafter, may be referred to as "autoxidation") even in the absence of a catalyst. Autoxidation not only reduces the yield of the intended product but also causes a vicious cycle in which the gas temperature is increased due to the heat of autoxidation and, consequently, autoxidation is accelerated. This may finally result in runaway combustion (hereinafter, may be referred to as "thermal runaway") and force the shutdown of the multitubular reactor.

One of the methods for preventing autoxidation is to reduce the concentration at which the raw material, that is, propylene or isobutylene, is fed to a multitubular reactor and the amount of the raw material fed. However, since this method reduces the amount of production relative to the size of a manufacturing facility, that is, productivity, this method is not preferable for commercial manufacturing, in which importance is placed on cost-effectiveness.

Another method for preventing the autoxidation is to reduce the residence time that a reaction product gas spends in a multitubular reactor. The larger the residence time of the gas in a multitubular reactor, the higher the degree of autoxidation and the greater the increase in the gas temperature which is caused by the autoxidation. Therefore, reducing residence time limits the degree of autoxidation and the increase in the gas temperature which is caused by the autoxidation.

PTL 1 discloses a method in which a flow straightener having, for example, a cone-like shape is disposed in a portion of a multitubular reactor from which a reaction product gas is derived in order to avoid the reaction product gas from building up in the reaction product gas derivation portion and thereby prevent a rapid temperature rise caused by decomposition of (meth)acrolein and the shutdown of the multitubular reactor which is caused by the rapid temperature rise.

Still another method for preventing the autoxidation is to slow the autoxidation to a degree at which any problem does not occur substantially, by rapidly cooling the reaction product gas discharged from the reactor.

PTL 2 discloses a method in which an acrolein-containing gas produced by the vapor-phase catalytic oxidation of propylene is rapidly cooled to 280° C. or less in order to prevent autoxidation.

Another issue of the vapor-phase catalytic oxidation performed using a multitubular reactor is the blockage of reaction tubes. An increase in the degree of blockage of reaction tubes results in a reduction in the amount of production. Feeding a required amount of raw material mixture gas to each of the reaction tubes in order to prevent the above issue requires an excessively high feed pressure. If the feed pressure exceeds the capacity of the facility, it is forced to shutdown.

One of the most common reasons for the blockage of reaction tubes is sedimentation of carbides (hereinafter, may be referred to as "coke"). Although the sedimentation of carbides (hereinafter, may be referred to as "coking") is reduced by changing the operation conditions, it is difficult to completely prevent coking; it is necessary to periodically remove coking (hereinafter, may be referred to as "decoking") by passing an oxygen-containing gas through the tubes.

NPL 1 discloses a method in which decoking of carbides accumulated in a reactor is performed by combustion at 350° C. to 500° C. while the oxygen concentration in the gas passed through the reactor is gradually increased.

PTL 1: JP2005-325043A

PTL 2: JP-56-73041A

NPL 1: Chemical Engineering/Jan. 18, 1988, p. 111-114

The autoxidation prevention method, coking prevention method, and decoking method that are known in the related art are not capable of preventing an increase in the pressure drop and blockage of a multitubular reactor with time to a sufficient degree in some cases.

As a result of studies of the reasons for the above issue, the following facts were found.

The catalyst used for performing the vapor-phase catalytic oxidation of propylene or isobutylene in order to commercially produce (meth)acrolein and (meth)acrylic acid commonly includes molybdenum oxide. Although molybdenum oxide has a low vapor pressure, it is likely to form a hydrate in the presence of water vapor. A hydrate of molybdenum oxide is likely to have a high vapor pressure.

It is considered that the presence of water vapor is advantageous in the vapor-phase catalytic oxidation of propylene or isobutylene. Since, for example, water is produced by the vapor-phase catalytic oxidation as a by-product and water vapor may be used as an inert gas in order to prevent the explosive composition of the raw material mixture gas introduced to a multitubular reactor, the reaction product gas produced subsequent to the vapor-phase catalytic oxidation may include 10% to 50% by volume of water vapor.

Thus, the reaction product gas present in the multitubular reactor includes molybdenum oxide having an increased vapor pressure as a result of being hydrated in the presence of water vapor, at a concentration of a few parts per billion to a few parts per million.

Thus, upon the reaction product gas being rapidly cooled, the molybdenum oxide included in the reaction product gas partially precipitates and the precipitates of molybdenum oxide and the like increase the pressure drop of the multitubular reactor with time and may finally cause blockage.

SUMMARY OF INVENTION

An object of the present invention is to provide a method for producing (meth)acrolein and (meth)acrylic acid by vapor-phase catalytic oxidation in the presence of a catalyst including molybdenum oxide with a multitubular reactor including a plurality of reaction tubes each including a reaction zone and a cooling zone, in which the reaction product gas is cooled to a sufficient degree and an increase in the pressure drop of the reaction tubes with time is reduced.

The inventors of the present invention inspected the inside of the reaction tubes of the multitubular reactor in which the pressure drop was increased in detail and consequently found that, in the reaction tubes in which the pressure drop was increased, the positions at which precipitates including molybdenum oxide were precipitated were accumulated at specific portions of the cooling zone of each reaction tube. In order to disperse the positions at which the precipitates are precipitated, the size of the filler used for the cooling zone was studied. As a result, it was found that the positions at which precipitates including molybdenum oxide are precipitated in the cooling zone may be greatly affected by the size of the filler. Thus, the method according to the present invention in which the increase in the pressure drop of the reaction tubes with time can be limited by using a filler having specific dimensions for the cooling zone was devised.

The summary of the present invention is as follows.

[1] A method for producing (meth)acrolein by vapor-phase catalytic oxidation of propylene or isobutylene in a multitubular reactor including a plurality of reaction tubes, the reaction tubes each including a reaction zone filled with a catalyst including molybdenum oxide and a cooling zone filled with an inert substance, wherein a temperature of a heat medium that flows outside the cooling zone is lower than a temperature of a heat medium that flows outside the reaction zone, and wherein the inert substance includes an inert substance having a major-axis length that is equal to or more than 1.7 times a major-axis length of the catalyst.

[2] The method for producing (meth)acrolein according to [1], wherein the inert substance includes an inert substance having a thermal conductivity represented by Formula (1) below.

$$\text{Thermal conductivity of inert substance} \leq \text{Thermal conductivity of molybdenum oxide} \times 0.1 \quad (1)$$

[3] The method for producing (meth)acrolein according to [1] or [2], wherein the inert substance includes a ring-shaped inert substance.

[4] The method for producing (meth)acrolein according to [3], wherein an inside diameter of the ring-shaped inert substance is equal to or more than 1.0 times the major-axis length of the catalyst.

[5] The method for producing (meth)acrolein according to any one of [1] to [4], wherein the inert substance includes a porcelain inert substance.

[6] The method for producing (meth)acrolein according to any one of [1] to [5], wherein an inside diameter of each of the reaction tubes is equal to or more than 1.3 times and equal to or less than 2.5 times the major-axis length of the inert substance.

[7] The method for producing (meth)acrolein according to any one of [1] to [6], wherein the temperature of the heat medium that flows outside the cooling zone and the temperature of the heat medium that flows outside the reaction zone satisfy Formula (2) below.

$$\text{Temperature of heat medium that flows outside cooling zone (° C.)} \leq \text{Temperature of heat medium that flows outside reaction zone (° C.)} - 50\text{° C.} \quad (2)$$

A method for producing (meth)acrylic acid in which (meth) acrolein produced by the method for producing (meth) acrolein according to any one of [1] to [7] is converted to (meth)acrylic acid by vapor-phase catalytic oxidation.

Advantageous Effects of Invention

In the method for producing (meth)acrolein and the method for producing (meth)acrylic acid according to the present invention, a reaction product gas can be cooled to a sufficient degree. Furthermore, the positions at which the precipitates are precipitated in the cooling zone of each reaction tube can be dispersed widely. Consequently, the increase in the pressure drop of the reaction tubes with time can be limited.

DESCRIPTION OF EMBODIMENTS

The method according to the present invention is described in detail with reference to the attached drawings below. Note that the present invention is not limited by the following description. Various modification may be made within the scope of the invention.

Although the method for producing (meth)acrolein according to the present invention is primarily described below, the method for producing (meth)acrylic acid according to the present invention can be implemented similarly to the method for producing (meth)acrolein according to the present invention by further performing the vapor-phase catalytic oxidation of (meth)acrolein produced by vapor-phase catalytic oxidation.

Figure 1:
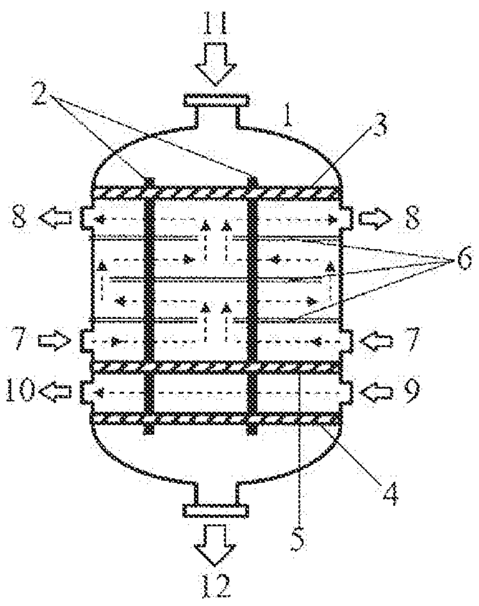
FIG. 1 is a schematic diagram illustrating reaction tubes included in a multitubular reactor and pathways disposed around the reaction tubes along which heat media are circulated.

FIG. 1 is a schematic diagram illustrating reaction tubes included in a multitubular reactor (vertical multitubular reactor) with which the vapor-phase catalytic oxidation of propylene or isobutylene is performed in the method for producing (meth)acrolein according to the present invention and pathways disposed around the reaction tubes along which heat media are circulated.

In the shell 1 of the multitubular reactor, a plurality of reaction tubes 2 are vertically arranged in an upright position. The reaction tubes 2 are disposed between an inlet-side tube plate 3 and an outlet-side tube plate 4 that are disposed on the upper end- and lower end-sides of the shell 1, respectively, in a hanging manner and are fixed to the shell 1.

An intermediate tube plate 5 is disposed at a position that is between the inlet-side tube plate 3 and the outlet-side tube plate 4 and is close to the outlet-side tube plate 4, so as to be parallel to the inlet-side tube plate 3 and the outlet-side tube plate 4. Between the intermediate tube plate 5 and the inlet-side tube plate 3, three baffle plates 6 for channels are arranged parallel to the intermediate tube plate 5 and the inlet-side tube plate 3. The lowermost and uppermost of the baffle plates 6 for channels have an opening formed at the center thereof, through which a heat medium can be passed. A gap through which a heat medium can be passed is formed between the periphery of the baffle plate 6 for channels which is disposed between the lowermost and uppermost baffle plates 6 for channels and the shell 1.

By the intermediate tube plate 5 and the baffle plates 6 for channels, in order to heat the reaction zones of the reaction tubes 2, a heat medium (hereinafter, may be referred to as "heat medium for heating") introduced from a heat medium feed channel 7 formed in the outer peripheral surface of the lower portion of the shell 1 flows between the intermediate tube plate 5 and the lowermost baffle plate 6 for channels, then flows upward through the opening of this baffle plate 6 for channels into the space above this baffle plate 6 for channels, subsequently flows between the lowermost baffle plate 6 for channels and the intermediate baffle plate 6 for channels, then flows upward between the shell 1 and the periphery of the intermediate baffle plate 6 for channels, subsequently flows between the intermediate baffle plate for channels and the uppermost baffle plate 6 for channels, then flows upward through the opening formed at the center of the uppermost baffle plate 6 for channels into the space above this baffle plate 6 for channels, subsequently flows between the baffle plate 6 for channels and the inlet-side tube plate 3, and is then drawn from a heat medium draw channel 8 formed in the peripheral surface of the upper portion of the shell 1. While the heat medium for heating is circulated in the above-described manner, the reaction zones of the reaction tubes 2 (portions of the reaction tubes 2 which extend between the inlet-side tube plate 3 and the intermediate tube plate 5) are heated.

On the other hand, in order to cool the cooling zones of the reaction tubes 2, a heat medium (hereinafter, may be referred to as "heat medium for cooling") introduced from a heat medium feed channel 9 formed in the peripheral surface of the lower portion of the shell 1 flows between the intermediate tube plate 5 and the outlet-side tube plate 4 and is then drawn from a heat medium draw channel 10 formed in the peripheral surface of the shell 1 on the opposite side. Meanwhile, the cooling zones of the reaction tubes 2 (portions of the reaction tubes 2 which extend between the intermediate tube plate 5 and the outlet-side tube plate 4) are cooled.

As described above, the reaction zone and the cooling zone are formed in each of the reaction tubes 2 continuously in the longitudinal direction (the direction in which the raw material mixture gas flows). The reaction zones of the reaction tubes 2 are filled with a catalyst including molybdenum oxide (hereinafter, may be referred to as "catalyst"). The cooling zones are filled with an inert substance.

The raw material mixture gas fed from a reactor inlet 11 is subjected to vapor-phase catalytic oxidation with the catalyst charged in the reaction zones of the reaction tubes 2 to form a reaction product gas that includes (meth)acrolein. The reaction product gas is cooled in the cooling zones of the reaction tubes 2 and then discharged from a reactor outlet 12.

The raw material mixture gas is a gas prepared by mixing a raw material, that is, propylene or isobutylene, with, for example, an oxygen-containing gas, such as air, and an inert gas, such as water vapor. The proportions of the above gas components are set appropriately in accordance with the reaction conditions and the like.

Figure 2:
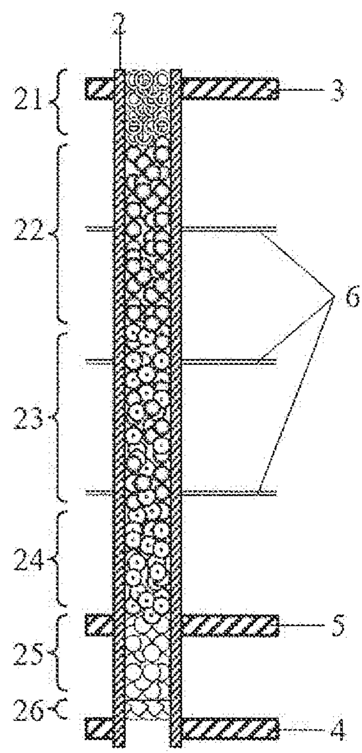
FIG. 2 is a schematic diagram illustrating the specification with which a catalyst and an inert substance are charged in the reaction tubes.

FIG. 2 is a schematic diagram illustrating the specification with which the catalyst and the inert substance are charged in the reaction tubes of the multitubular reactor illustrated in FIG. 1.

The layer charged in each reaction tube 2 is constituted by, in order closest to the inlet of the multitubular reactor, that is, in order in which the raw material mixture gas passes, a preheat layer 21 that heats the raw material mixture gas, three catalyst layers 22 to 24 (reaction zone) that convert the heated raw material mixture gas into a reaction product gas by vapor-phase catalytic oxidation, a rapid cooling layer 25 (cooling zone) that cools the reaction product gas, and a catalyst stopper 26 disposed at the lower end of the reaction tube. The preheat layer and the rapid cooling layer (cooling zone) are each filled with an inert substance. The catalyst layers (reaction zone) are filled primarily with a catalyst. The inert substance is a substance that does not contribute to vapor-phase catalytic oxidation.

In the present invention, the inert substance charged in the rapid cooling layer (cooling zone) 25 includes an inert substance that satisfies the requirement (1) below and preferably includes an inert substance that further satisfies the requirements (2) to (6) below.

Note that an inert substance that includes the inert substance that satisfies the requirement below is an inert substance in which the content of the inert substance that satisfies the requirement below is preferably 80% by mass or more, is more preferably 90% by mass or more, and is particularly preferably 95% to 100% by mass of the total amount of the inert substance.

(1) The Major-Axis Length of the Inert Substance is Equal to or More than 1.7 Times the Major-Axis Length of the Catalyst In the present invention, it is essential that the inert substance charged in the rapid cooling layer (cooling zone) include an inert substance such that the major-axis length of the inert substance is equal to or more than 1.7 times the major-axis length of the catalyst charged in the catalyst layers (reaction zone), that is, the ratio of the major-axis length of the inert substance to the major-axis length of the catalyst is 1.7 or more.

When the ratio of the major-axis length of the inert substance to the major-axis length of the catalyst is 1.7 or more, the amount of area in which the gas is cooled per unit volume of the layer is reduced and, accordingly, a reduction in the gas temperature can be limited. Consequently, it becomes possible to prevent the accumulation of the positions at which the precipitates are precipitated.

The term "major-axis length" used herein refers to the length of the interval between two parallel plates that sandwich an object which is measured at the position at which the interval between the two plates is maximum.

In order to reduce the amount of area in which the gas is cooled, the ratio of the major-axis length of the inert substance to the major-axis length of the catalyst is preferably 1.8 or more and is more preferably 1.9 or more.

Since it is difficult to increase the ratio of the major-axis length of the inert substance to the major-axis length of the catalyst to an excessive degree in terms of the design of the multitubular reactor, the above ratio is commonly 3.4 or less and is preferably 3.3 or less.

(2) The Thermal Conductivity of the Inert Substance is Equal to or Less than 0.1 Times the Thermal Conductivity of Molybdenum Oxide The inert substance charged in the rapid cooling layer (cooling zone) preferably includes an inert substance having a thermal conductivity represented by Formula (1) below.

$$\text{Thermal conductivity of inert substance} \leq \text{Thermal conductivity of molybdenum oxide} \times 0.1 \quad (1)$$

When the inert substance that satisfies Formula (1) above is charged in the rapid cooling layer (cooling zone), it becomes possible to widely disperse the positions at which precipitates are precipitated in the rapid cooling zone (cooling zone) of each reaction tube and, consequently, the increase in the pressure drop of the reaction tube with time can be limited.

When the reaction product gas is cooled in the rapid cooling layer (cooling zone), molybdenum oxide included in the reaction product gas partially precipitates on the surface of the inert substance. In the case where the thermal conductivity of the inert substance satisfies Formula (1) above, the total heat-transfer coefficient of the rapid cooling layer (cooling zone) can be maintained to be low unless the amount of molybdenum oxide precipitated is large. That is, it becomes possible to prevent a vicious cycle in which the precipitation of molybdenum oxide in the rapid cooling layer (cooling zone) increases the total heat-transfer coefficient of the rapid cooling layer (cooling zone), the cooling rate is increased accordingly, and further precipitation of molybdenum oxide is caused consequently.

From the above-described viewpoints, the thermal conductivity of the inert substance more preferably satisfies Formula (1A) below and further preferably satisfies Formula (1B) below.

$$\text{Thermal conductivity of inert substance} \leq \text{Thermal conductivity of molybdenum oxide} \times 0.095 \quad (1A)$$

$$\text{Thermal conductivity of inert substance} \leq \text{Thermal conductivity of molybdenum oxide} \times 0.090 \quad (1B)$$

Since it is necessary to cool the gas before it reaches the outlet of the rapid cooling layer for preventing the autoxidation of acrolein, the thermal conductivity of the inert substance commonly satisfies Formula (1C) below with respect to the thermal conductivity of molybdenum oxide.

$$\text{Thermal conductivity of inert substance} \geq \text{Thermal conductivity of molybdenum oxide} \times 0.01 \quad (1C)$$

(3) Ring-Shaped Inert Substance

The inert substance charged in the rapid cooling layer (cooling zone) preferably includes a ring-shaped inert substance.

When the inert substance has a ring shape, the porosity of the charged layer can be maintained to be high and the reaction product gas is allowed to flow smoothly. Furthermore, the mechanical strength of the inert substance can be maintained while an adequate thermal conductivity is maintained.

(4) The Inside Diameter of the Ring-Shaped Inert Substance is Equal to or More than 1.0 Times the Major-Axis Length of the Catalyst The inside diameter of the ring-shaped inert substance is preferably equal to or more than 1.0 times the major-axis length of the catalyst. That is, the ratio of the inside diameter of the inert substance to the major-axis length of the catalyst is preferably 1.0 or more. The above ratio is more preferably 1.01 or more, is further preferably 1.02 or more, is preferably 1.5 or less, and is more preferably 1.4 or less.

When the ratio of the inside diameter of the inert substance to the major-axis length of the catalyst falls within the above range, the porosity of the cooling zone can be maintained to be high and the reaction product gas is allowed to flow smoothly. Furthermore, the penetration of the catalyst into the cooling zone can be prevented while an adequate thermal conductivity is maintained. Consequently, it becomes possible to cool the reaction product gas with efficiency.

(5) Porcelain Inert Substance

The inert substance charged in the rapid cooling layer (cooling zone) preferably includes a porcelain inert substance. It is more preferable that all of the inert substances be porcelain inert substances.

When the inert substance includes a porcelain inert substance, it becomes possible to prevent a vicious cycle in which the cooling rate is increased with time due to the precipitation of molybdenum oxide and the like in the rapid cooling layer (cooling zone) and, consequently, the degree of blockage is further increased.

(6) The Inside Diameter of Each Reaction Tube is Equal to or More than 1.3 Times and Equal to or Less than 2.5 Times the Major-Axis Length of the Inert Substance The inside diameter of each of the reaction tubes included in the multitubular reactor is preferably equal to or more than 1.3 times and equal to or less than 2.5 times the major-axis length of the inert substance. That is, the ratio of the inside diameter of each reaction tube to the major-axis length of the inert substance is preferably 1.3 to 2.5. The above ratio is more preferably 1.4 or more and is further preferably 1.5 or more. As for the upper limit, the above ratio is more preferably 2.2 or less and is further preferably 2.0 or less.

When the ratio of the inside diameter of each reaction tube to the major-axis length of the inert substance falls within the above range, the cooling zone of the reaction tube has a sufficient porosity. Furthermore, it becomes possible to reduce variations in charge density which occur when the inert substance is repeatedly charged, discharged, and again charged.

In the present invention, the temperature of the heat medium for cooling which flows outside the cooling zones of the reaction tubes is lower than the temperature of the heat medium for heating which flows outside the reaction zones of the reaction tubes. The temperatures of these heat media preferably satisfy Formula (2) below.

$$\text{Temperature of heat medium that flows outside cooling zone } (^\circ\text{ C.}) \leq \text{Temperature of heat medium that flows outside reaction zone } (^\circ\text{ C.}) - 50^\circ\text{ C.} \quad (2)$$

When the temperatures of the heat media satisfy Formula (2) above, the reaction product gas can be cooled with efficiency.

It is more preferable that the temperature of the heat medium for cooling be lower than the temperature of the heat medium for heating by 60° C. or more. Specifically, it is preferable that the temperature of the heat medium for cooling be 200° C. to 280° C. and the temperature of the heat medium for heating be 300° C. to 360° C.

The catalyst layers (reaction zone) are filled primarily with a catalyst. In order to reduce the likelihood of the raw material mixture gas reacting in the catalyst layers (reaction zone), into which the raw material mixture gas passes subsequent to the preheat layer, to an excessive degree, a mixture of the catalyst and the inert substance may be charged into the portion of the catalyst layers (reaction zone) which is in the vicinity of the preheat layer. In such a case, it is preferable to increase the mixing ratio of the inert substance to the catalyst. In the case where only the catalyst is charged, it is preferable to charge a catalyst having a relatively low reactivity.

The inert substance charged in the preheat layer is not limited and may be any inert substance that allows the raw material mixture gas to be heated. The inert substance that is mixed with the catalyst and charged into the reaction zone is not limited and may be any inert substance that can be readily mixed with the catalyst and that has substantially the same size as the catalyst. Regardless of whether the inert substance is charged into the preheat layer or the reaction zone, the material constituting the inert substance is not limited to porcelain and may be silicon carbide, ceramic balls, stainless steel, or the like. The shape of the inert substance can be selected from various shapes, such as a spherical shape, a solid-cylindrical shape, a hollow-cylindrical shape, a saddle shape, and a ring shape.

Figure 3:
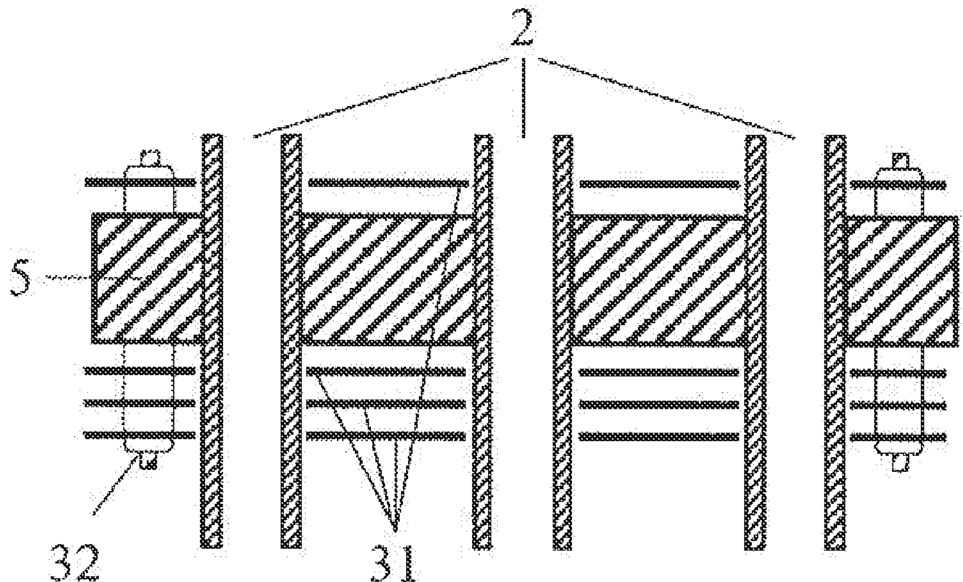
FIG. 3 is a schematic cross-sectional view of a portion of the multitubular reactor which is in the vicinity of an intermediate tube plate.

FIG. 3 is a schematic cross-sectional view of a portion of the multitubular reactor which is in the vicinity of the intermediate tube plate 5. Since the temperature of the heat medium for cooling which flows outside the cooling zones is lower than the temperature of the heat medium for heating which flows outside the reaction zones as described above, the intermediate tube plate 5 is subjected to a thermal stress. In FIG. 3, in order to reduce the above thermal stress, baffle plates 31 for retention are disposed above and below the intermediate tube plate 5 and fixed in place with fixtures 32.

The thermal conductivity of the heat media is commonly equal to or less than one hundredth of the thermal conductivity of the intermediate tube plate 5. Arranging the baffle plates 31 for retention above one or both of the surfaces of the intermediate tube plate 5 causes a temperature gradient to be created in the heat medium held by the intermediate tube plate 5 and the baffle plates 31 for retention, in the longitudinal direction of the reaction tubes 2. This does not create excessive impacts because the heat medium held by the intermediate tube plate 5 and the baffle plates 31 for retention is flowable.

Since the temperature of the heat medium present between the baffle plates 31 for retention varies in the longitudinal direction of the reaction tubes 2, the temperature inside the reaction tubes 2 also varies greatly in the vicinity of the boundary between the reaction zones and the cooling zones. Therefore, in the case where precipitates are formed as a result of the reaction product gas being rapidly cooled, the accumulation of the positions at which the precipitation occurs may be prevented by increasing the number of the baffle plates 31 for retention or increasing the intervals at which the baffle plates 31 for retention are arranged. However, in such a case, it becomes necessary to increase the length of the reaction tubes 2. This may lead to increases in the size of the reactor and the equipment costs.

Figure 4:
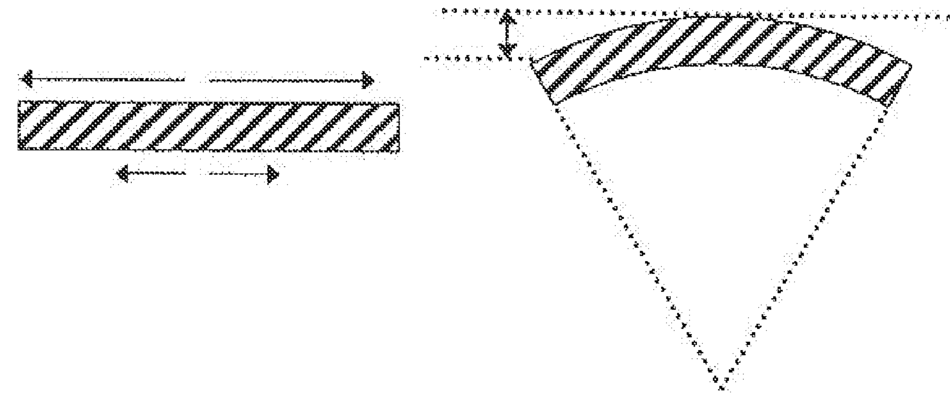
FIG. 4 is a conceptual diagram illustrating the distortion of the intermediate tube plate which is caused by thermal expansion.

FIG. 4 is a conceptual diagram illustrating the distortion of the intermediate tube plate 5 which is caused by thermal expansion. The degree of expansion or contraction that occurs due to temperature change varies by metal type. The degree of expansion or contraction of general-purpose steels is about one hundred thousandth per degree Celsius. That is, even in the case where the temperature is increased or reduced by 100° C., the degree of expansion or contraction is only about one thousandth, which poses little problem for small apparatuses. However, assuming that the shell of the multitubular reactor have a diameter of 5 m and the intermediate tube plate 5 have a thickness of 10 cm, the both edges of the intermediate tube plate 5 are considered to rise 3 cm theoretically. Thus, it is necessary to address this issue. Examples of the countermeasure include forming a firm structure capable of withstanding the thermal stress; and reducing the difference in temperature between the front and rear surfaces of the intermediate tube plate 5 by using the baffle plates 31 for retention and the like.

In the vapor-phase catalytic oxidation of propylene or isobutylene according to the present invention, (meth)acrolein and (meth)acrylic acid formed as a result of the (meth) acrolein being partially subjected to vapor-phase catalytic oxidation are produced. In addition, (meth)acrylic acid is produced by the vapor-phase catalytic oxidation of (meth) acrolein.

The raw material mixture gas fed to the multitubular reactor used for vapor-phase catalytic oxidation is primarily a mixed gas including propylene or isobutylene, a molecular oxygen-containing gas, and an inert gas, such as water vapor.

It is preferable that the concentration of propylene or isobutylene in the raw material mixture gas be 6% to 10% by mole, the amount of oxygen be 1.5 to 2.5 times by mole the amount of the propylene or isobutylene, and the amount of the inert gas be 0.8 to 5 times by mole the amount of the propylene or isobutylene. The raw material mixture gas introduced is divided into and passed through the reaction tubes and undergoes the reaction in the presence of the catalyst charged in the reaction tubes.

Examples of the oxygen-containing gas include air and an oxygen-containing waste gas produced in other manufacturing facilities. The oxygen-containing gas is preferably air.

Examples of the inert gas include water vapor, nitrogen, and carbon dioxide, which are industrially available at low costs. A mixed gas separated and recovered from the gas used for vapor-phase catalytic oxidation can also be reused as an inert gas.

Examples of the catalyst include a catalyst suitable for the former reaction in which (meth)acrolein is produced by the vapor-phase catalytic oxidation of propylene or isobutylene and a catalyst suitable for the latter reaction in which (meth)acrylic acid is produced by the vapor-phase catalytic oxidation of (meth)acrolein. In both of the above reactions, a catalyst including molybdenum oxide is used.

The catalyst for the former reaction is preferably the catalyst represented by Formula (I) below.

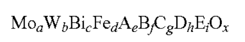

$$Mo_aW_bBi_cFe_dA_eB_fC_gD_hE_iO_x \quad (I)$$

In Formula (I) above, A represents at least one element selected from nickel and cobalt; B represents at least one element selected from sodium, potassium, rubidium, cesium, and thallium; C represents at least one element selected from alkaline-earth metals; D represents at least one element selected from phosphorus, tellurium, antimony, tin, cerium, lead, niobium, manganese, arsenic, boron, and zinc; E represents at least one element selected from silicon, aluminum, titanium, and zirconium; O represents oxygen; a, b, c, d, e, f, g, h, i, and x represent the atomic ratios of Mo, W, Bi, Fe, A, B, C, D, E, and O, respectively; in the case where a=12, $0 \leq b \leq 10$, $0 < c \leq 10$ (preferably $0.1 \leq c \leq 10$), $0 < d \leq 10$ (preferably $0.1 \leq d \leq 10$), $2 \leq e \leq 15$, $0 < f \leq 10$ (preferably $0.001 \leq f \leq 10$), $0 \leq g \leq 10$, $0 \leq h \leq 4$, and $0 \leq i \leq 30$; and x is a value determined in accordance with the oxidation states of the above elements.

The catalyst for the latter reaction is preferably the catalyst represented by Formula (II) below.

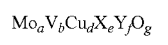

$$Mo_aV_bCu_dX_eY_fO_g \quad (II)$$

In Formula (II) above, X represents at least one element selected from Mg, Ca, Sr, and Ba; Y represents at least one element selected from Ti, Zr, Ce, Cr, Mn, Fe, Co, Ni, Zn, Nb, Sn, Sb, Pb, and Bi; O represents oxygen; a, b, c, d, e, f, and g represent the atomic ratios of Mo, V, W, Cu, X, Y, and O, respectively; in the case where a=12, $2 \leq b \leq 14$, $0 \leq c \leq 12$, $0 < d \leq 6$, $0 \leq e \leq 3$, and $0 \leq f \leq 3$; and g is a value determined in accordance with the oxidation states of the above elements.

The above catalyst is produced by, for example, the methods disclosed in JP-S63-54942A, JP-H6-13096A, and JP-H6-38918A.

The catalyst used in the present invention may be a molded catalyst formed by extrusion molding or tablet compression or a supported catalyst formed by supporting an oxide that serves as a catalytic component on an inert carrier composed of silicon carbide, alumina, zirconium oxide, titanium oxide, or the like. In the case where a supported catalyst is used, the composition of the catalyst which is represented by the above formula is the composition of the catalyst excluding the carrier.

The shape of the catalyst used in the present invention is not limited and may be any of a spherical shape, a solid-cylindrical shape, a hollow-cylindrical shape, a star shape, a ring shape, an indefinite shape, and the like.

The major-axis length of the catalyst is commonly about 5.0 to 7.0 mm.

EXAMPLES

The present invention is described further specifically with reference to Test Example, Examples, and Comparative Examples, below.

Test Example 1

Acrolein was produced using propylene as a raw material with the vertical multitubular reactor illustrated in FIG. 1, in which the number of the reaction tubes 2 was 20,000. Three baffle plates 31 for retention as illustrated in FIG. 3 were disposed below the intermediate tube plate 5. The acrolein produced in the multitubular reactor was converted into acrylic acid in the subsequent step.

A catalyst was charged into each of the reaction tubes (inside diameter: 27 mm) 2 of the multitubular reactor so as to form three catalyst layers (reaction zone) 22 to 24 as illustrated in FIG. 2. The catalyst charged was a ring-shaped catalyst (outside diameter: 5 mm, inside diameter: 2 mm, height: 3 mm, major-axis length: 5.8 mm) formed by tablet compression. The catalyst had a composition of $Mo_{12}Bi_3Fe_{0.5}Ni_{2.5}Co_{2.5}Na_{0.4}K_{0.1}B_{0.4}Si_{24}$.

Porcelain Raschig rings having an outside diameter of 6.4 mm, an inside diameter of 3.5 mm, and a height of 6.4 mm (major-axis length: 9.1 mm) were charged into a rapid cooling layer (cooling zone) 25. The thermal conductivity of the porcelain Raschig rings was 1 to 1.5 W/mK, which was 0.04 to 0.06 times the thermal conductivity of molybdenum oxide (24 W/mK). The major-axis length of the porcelain Raschig rings was 1.6 times the major-axis length of the catalyst.

Subsequent to the charging of the catalyst and the porcelain Raschig rings, 500 reaction tubes were selected. A certain amount of dry air was passed through the reaction tubes, and the pressure drop prior to the start of operation (initial state) was measured. The average of the pressure drops of the 500 reaction tubes was 5 kPa.

The catalyst and the porcelain Raschig rings were removed from the inlet of one of the reaction tubes which had a pressure drop of 5 kPa, which was equal to the above average, in stages and the pressure drops were measured. The pressure drops measured were:

(1) the pressure drop across the section extending from the inlet of the reaction tube to the outlet of the rapid cooling layer, (2) the pressure drop across the section extending from the upper portion of the catalyst layer to the outlet of the rapid cooling layer which is measured after the catalyst had been removed, (3) the pressure drop across the section extending from the upper portion of the rapid cooling layer to the outlet of the rapid cooling layer which is measured after the porcelain Raschig rings had been further removed.

The above pressure drops were the pressures measured at the inlet of the reaction tube when dry air was passed from the inlet of the reaction tube at 1000 NL/H.

The temperature of the heat medium for heating which was measured in the heat medium feed channel was 315° C. to 325° C. The temperature of the heat medium for cooling which was measured in the heat medium feed channel was 235° C. to 245° C. The temperature of the gas that had been passed through the rapid cooling layer was 235° C. to 245° C., which was the same as that of the heat medium for cooling.

An operation for producing acrolein by the vapor-phase catalytic oxidation of propylene was continuously conducted for 11 months. Subsequently, the operation was stopped for one month for maintenance work. Then, an operation for producing acrolein by the vapor-phase catalytic oxidation of propylene was continuously conducted for another 11 months. Subsequently (two years later), air heated at about 400° C. was passed through all the reaction tubes in order to perform decoking of all the reaction tubes. After the reaction tubes had been cooled, they entered into the multitubular reactor and measured the pressure drops of the 500 reaction tubes that had been subjected to the measurement of pressure drop prior to the start of operation (initial state) in the same manner as described above. Two reaction tubes that had the highest pressure drops were selected. Subsequently, the catalyst and the porcelain Raschig rings were removed from the inlet of each of the two reaction tubes in stages and the pressure drops were measured in the same manner as described above.

Figure 5:
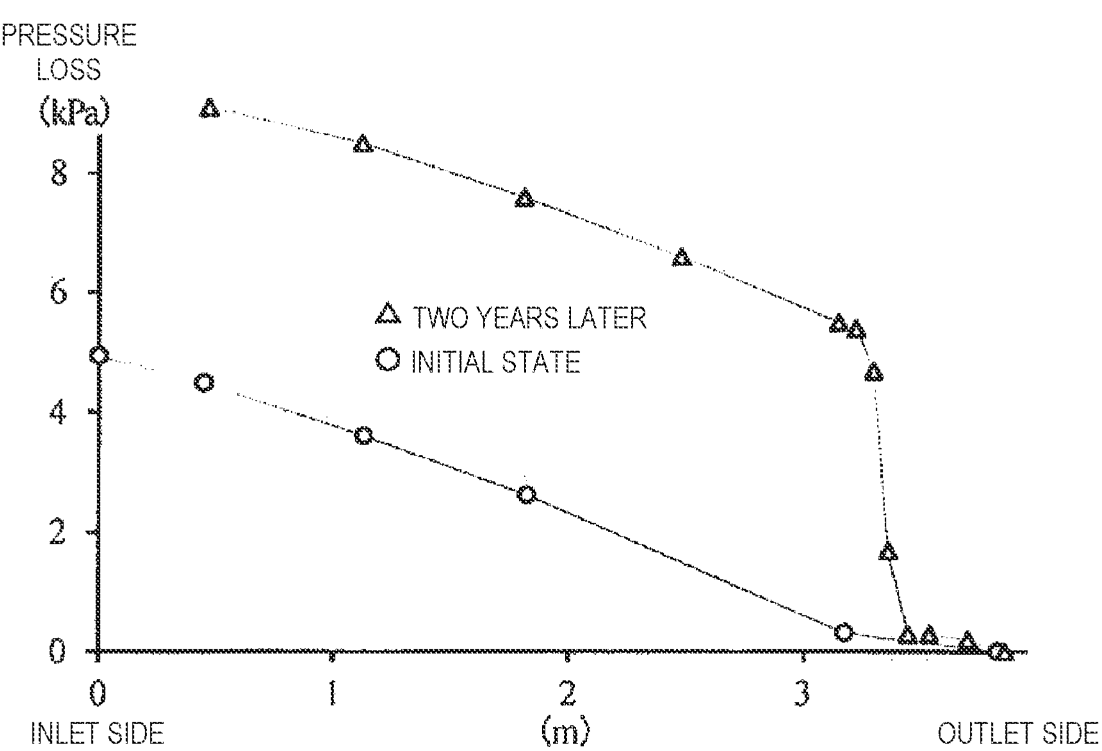
FIG. 5 is a graph illustrating the averages of the pressure drops of the reaction tubes which are measured in Test Example 1 prior to and subsequent to the operation for producing acrolein.

FIG. 5 illustrates the averages of the pressure drops over the entire reaction tubes which were measured prior to the start of operation (initial state) and subsequent to the operation for producing acrolein (two years later).

Figure 6:
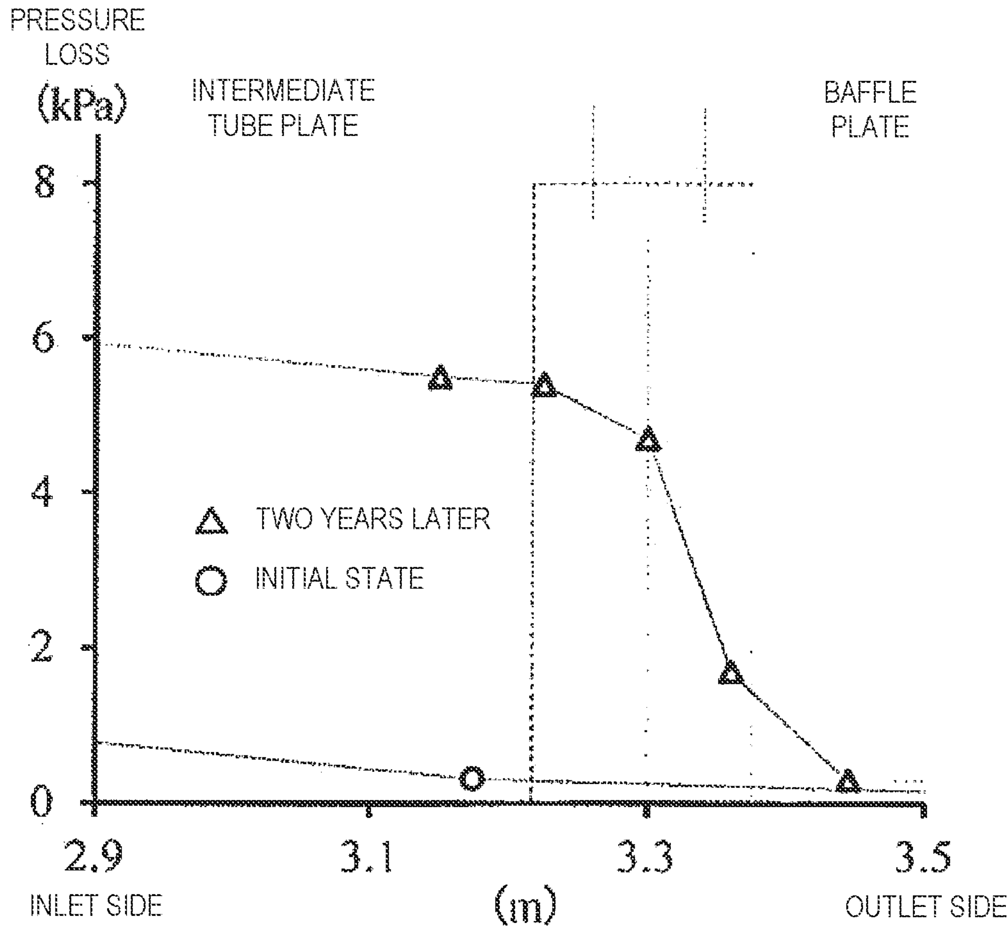
FIG. 6 is a graph illustrating a portion of FIG. 5 which corresponds to the outlet of the reaction zone of the reaction tubes and the cooling zone of the reaction tubes in a magnified view.

FIG. 6 is a magnified view of a part of FIG. 5 which corresponds to the outlet of the reaction zone of the reaction tube (the position 2.9 m from the upper inlet of the reaction tube) and the cooling zone of the reaction tube (to the position 3.5 m from the upper inlet of the reaction tube).

Furthermore, a fiberscope was inserted into each of the selected two reaction tubes in order to observe the inside of the reaction tube.

As a result, it was found that the positions at which the difference between the pressure drops of the reaction tube measured prior to and subsequent to the start of operation was significantly large coincided with the positions at which precipitates were precipitated.

Specifically, the average pressure drop significantly varied at the portions corresponding to the intermediate tube plate and the baffle plates for retention as illustrated in FIG. 5, at which the temperature of the heat medium rapidly changed, and particularly at the portion corresponding to the baffle plates for retention. The results of the observation of the inside of each reaction tube with the fiberscope confirmed the presence of a glistening white thin-film and acicular crystals formed of molybdenum oxide which were accumulated at the inner wall surface of a portion of the cooling zone which was close to the reaction zone of the reaction tube. Furthermore, it was confirmed that a substance that was considered to be produced as a result of detachment of the acicular crystals was scattered in the porcelain Raschig rings present in the portion of the cooling zone which was close to the reaction zone of the reaction tube.

On the basis of the results of the observation, it is considered that the substance adhered to the portion of the cooling zone which was close to the reaction zone of the reaction tube (hereinafter, such a portion is referred to as "portion A") narrowed the channel. This presumably increased the linear velocity of the reaction product gas that passed through the portion A and consequently caused the adhered substance to spread to the downstream of the portion A with time.

Example 1

All of the fillers including the catalyst were removed from five reaction tubes (inside diameter: 27 mm) included in a vertical multitubular reactor which had been subjected to decoking prior to periodic maintenance. A catalyst was charged into each of the five reaction tubes so as to form catalyst layers (reaction zone) 22 to 24. The catalyst charged was a ring-shaped catalyst (outside diameter: 5 mm, inside diameter: 2 mm, height: 3 mm, major-axis length: 5.8 mm) formed by tablet compression. The catalyst had a composition of $Mo_{12}Bi_3Fe_{0.5}Ni_{2.5}Co_{2.5}Na_{0.4}K_{0.1}B_{0.4}Si_{24}$.

Porcelain Raschig rings having an outside diameter of 10.0 mm, an inside diameter of 6.0 mm, and a height of 10.0 mm (major-axis length: 14.1 mm) were charged into a rapid cooling layer (cooling zone) 25. The thermal conductivity of the porcelain Raschig rings was 1 to 1.5 W/mK, which was 0.04 to 0.06 times the thermal conductivity of molybdenum oxide (24 W/mK). The major-axis length of the porcelain Raschig rings was 2.4 times the major-axis length of the catalyst. Prior to the operation for producing acrolein, a certain amount of dry air was passed through the reaction tubes and the pressure drop of each of the reaction tubes was measured. The average of the pressure drops of all the reaction tubes was considered as the pressure drop prior to the production operation.

The temperature of the heat medium for heating which was measured in the heat medium feed channel was 315° C. to 325° C. The temperature of the heat medium for cooling which was measured in the heat medium feed channel was 235° C. to 245° C. The acrolein produced in the multitubular reactor was converted into acrylic acid in the subsequent step.

Acrolein was continuously produced by the vapor-phase catalytic oxidation of propylene for 11 months with the vertical multitubular reactor, and an operation for producing acrylic acid was conducted in the subsequent step. Subsequently, the operation was stopped for one month for maintenance work. Then, acrolein was continuously produced by the vapor-phase catalytic oxidation of propylene for another 11 months, and an operation for producing acrylic acid was conducted in the subsequent step. Subsequently (two years later), after decoking had been performed, the pressure drop of each of the reaction tubes was measured. The pressure drop measured was the pressure drop across the section extending from the inlet of the reaction tube to the outlet of the rapid cooling layer and was the pressure measured at the inlet of the reaction tube when dry air was passed from the inlet of the reaction tube at 1000 NL/H. The average of the pressure drops of all the reaction tubes was considered as the pressure drop subsequent to the production operation.

An increase in the pressure drop of the reaction tubes which was measured after 1 year of acrolein production relative to the pressure drop measured prior to the acrolein production was 1.1 kPa. An increase in the pressure drop of the reaction tubes which was measured after 2 years of acrolein production relative to the pressure drop measured prior to the acrolein production was 1.3 kPa. The temperature of the gas that had been passed through the rapid cooling layer was 235° C. to 245° C., which was the same as that of the heat medium for cooling.

Comparative Example 1

Acrolein was produced by the vapor-phase catalytic oxidation of propylene under the same conditions as in Example 1, except that the inert substance charged into the rapid cooling layer (cooling zone) 25 was changed to porcelain Raschig rings having an outside diameter of 6.4 mm, an inside diameter of 3.5 mm, and a height of 6.4 mm (major-axis length: 9.1 mm, the ratio of the major-axis length of the inert substance to the major-axis length of the catalyst: 1.6). Then, an operation for producing acrylic acid was conducted in the subsequent step. As in Example 1, prior to the operation for producing acrolein, a certain amount of dry air was passed through the reaction tubes and the pressure drop of each of the reaction tubes was measured. The average thereof was considered as the pressure drop prior to the production operation. Similarly, the pressure drop subsequent to the production operation was determined by averaging the pressure drops of all the reaction tubes.

An increase in the pressure drop of the reaction tubes which was measured after 1 year of acrolein production relative to the pressure drop measured prior to the acrolein production was 1.3 kPa. An increase in the pressure drop of the reaction tubes which was measured after 2 years of acrolein production relative to the pressure drop measured prior to the acrolein production was 1.9 kPa. The temperature of the gas that had been passed through the rapid cooling layer was 235° C. to 245° C., which was the same as that of the heat medium for cooling.

Example 2

Acrolein was produced by the vapor-phase catalytic oxidation of propylene under the same conditions as in Example 1, except that the inert substance charged into the rapid cooling layer (cooling zone) 25 was changed to porcelain Raschig rings having an outside diameter of 12.0 mm, an inside diameter of 8.0 mm, and a height of 12.0 mm (major-axis length: 17.0 mm, the ratio of the major-axis length of the inert substance to the major-axis length of the catalyst: 2.9). Then, an operation for producing acrylic acid was conducted in the subsequent step. As in Example 1, prior to the operation for producing acrolein, a certain amount of dry air was passed through the reaction tubes and the pressure drop of each of the reaction tubes was measured. The average thereof was considered as the pressure drop prior to the production operation. Similarly, the pressure drop subsequent to the production operation was determined by averaging the pressure drops of all the reaction tubes.

An increase in the pressure drop of the reaction tubes which was measured after 1 year of acrolein production relative to the pressure drop measured prior to the acrolein production was 1.0 kPa. An increase in the pressure drop of the reaction tubes which was measured after 2 years of acrolein production relative to the pressure drop measured prior to the acrolein production was 1.1 kPa. The temperature of the gas that had been passed through the rapid cooling layer was 235° C. to 245° C., which was the same as that of the heat medium for cooling.

Comparative Example 2

Acrolein was produced by the vapor-phase catalytic oxidation of propylene under the same conditions as in Example 1, except that the inert substance charged into the rapid cooling layer (cooling zone) 25 was changed to stainless steel Raschig rings having an outside diameter of 6.35 mm, an inside diameter of 5.35 mm, and a height of 6.5 mm (major-axis length: 9.1 mm, the ratio of the major-axis length of the inert substance to the major-axis length of the catalyst: 1.6). Then, an operation for producing acrylic acid was conducted in the subsequent step. The thermal conductivity of the stainless steel Raschig rings was 14 W/mK, which was 0.58 times the thermal conductivity of molybdenum oxide (24 W/mK). As in Example 1, prior to the operation for producing acrolein, a certain amount of dry air was passed through the reaction tubes and the pressure drop of each of the reaction tubes was measured. The average thereof was considered as the pressure drop prior to the production operation. Similarly, the pressure drop subsequent to the production operation was determined by averaging the pressure drops of all the reaction tubes.

An increase in the pressure drop of the reaction tubes which was measured after 1 year of acrolein production relative to the pressure drop measured prior to the acrolein production was 0.9 kPa. An increase in the pressure drop of the reaction tubes which was measured after 2 years of acrolein production relative to the pressure drop measured prior to the acrolein production was 20.0 kPa. The temperature of the gas that had been passed through the rapid cooling layer was 235° C. to 245° C., which was the same as that of the heat medium for cooling. Since the stainless steel Raschig rings used as an inert substance had high thermal conductivity, it is considered that the degree of local precipitation of molybdenum oxide was increased with time and, consequently, the pressure drop was significantly increased two years later.

On the basis of the above results, it became clear that the increase in pressure drop over a long period of time can be markedly limited by filling the rapid cooling layer (cooling zone) with an inert substance having a major-axis length that is equal to or more than 1.7 times the major-axis length of the catalyst and a thermal conductivity that is equal to or less than 0.1 times that of molybdenum oxide.

Although the present invention has been described in detail with reference to specific aspects, it is apparent to a person skilled in the art that various alterations and modifications can be made therein without departing from the spirit and scope of the present invention.

The present application is based on Japanese Patent Application No. 2020-017679 filed on Feb. 5, 2020, which is incorporated herein by reference in its entirety.

REFERENCE SIGNS LIST

1 SHELL OF MULTITUBULAR REACTOR
2 REACTION TUBE

3 INLET-SIDE TUBE PLATE
4 OUTLET-SIDE TUBE PLATE
5 INTERMEDIATE TUBE PLATE
6 BAFFLE PLATE FOR CHANNELS
7 HEAT MEDIUM FEED CHANNEL
8 HEAT MEDIUM DRAW CHANNEL
9 HEAT MEDIUM FEED CHANNEL
10 HEAT MEDIUM DRAW CHANNEL
11 REACTOR INLET
12 REACTOR OUTLET
21 PREHEAT LAYER
22 CATALYST LAYER 1
23 CATALYST LAYER 2
24 CATALYST LAYER 3
25 RAPID COOLING LAYER (COOLING ZONE)
26 CATALYST STOPPER
31 BAFFLE PLATE FOR RETENTION
32 FIXTURE

The invention claimed is:

1. A method for producing (meth) acrolein, the method comprising:

oxidizing propylene or isobutylene by vapor-phase catalytic oxidation in a multitubular reactor comprising a plurality of reaction tubes, the reaction tubes each comprising (i) a reaction zone filled with a catalyst comprising molybdenum oxide and (ii) a cooling zone comprising an inert substance, wherein the catalyst has a spherical shape, a solid-cylindrical shape, a hollow-cylindrical shape, a star shape, and/or a ring shape, wherein a temperature of a heat medium that flows outside the cooling zone is lower than a temperature of a heat medium that flows outside the reaction zone, and wherein the inert substance has a major-axis length that is equal to or more than 1.7 times and equal to or less than 3.4 times a major-axis length of the catalyst, and wherein the substance has a thermal conductivity satisfying formula (1):

$$K_{IS} \leq K_{MO_x} \times 0.1, \quad (1)$$

wherein $K_{IS}$ is the thermal conductivity of the inert substance, and $K_{MOx}$ is the thermal conductivity of molybdenum oxide.

2. The method of claim 1, wherein the inert substance comprises a ring-shaped inert substance.

3. The method of claim 2, wherein an inside diameter of the ring-shaped inert substance is equal to or more than 1.0 times the major-axis length of the catalyst.

4. The method of claim 1, wherein the inert substance comprises a porcelain inert substance.

5. The method of claim 1, wherein an inside diameter of each of the reaction tubes is equal to or more than 1.3 times and equal to or less than 2.5times the major-axis length of the inert substance.

6. The method of claim 1, wherein the temperature of the heat medium that flows outside the cooling zone and the temperature of the heat medium that flows outside the reaction zone satisfy formula (2):

$$T_C \leq T_R - 50° \text{ C.} \quad (2)$$

wherein $T_C$ is the temperature of the heat medium that flows outside the cooling zone in ° C. and $T_R$ is the temperature of the heat medium that flows outside the reaction zone in ° C.

7. A method for producing (meth)acrylic acid, the method comprising, producing (meth)acrolein by the method of claim 1; and converting the (meth)acrolein to (meth)acrylic acid by vapor-phase catalytic oxidation.

8. The method of claim 1, wherein the inert substance is present in, but does not contribute to, vapor-phase catalytic oxidation.

9. The method of claim 1, wherein the major-axis length of the inert substance is equal to or more than 1.8 times and equal to or less than 3.3 times the major-axis length of the catalyst.

10. The method of claim 1, wherein the major-axis length of the inert substance is equal to or more than 1.9 times and equal to or less than 3.3 times the major-axis length of the catalyst.

11. The method of claim 1, wherein the inert substance is porcelain rings.

12. The method of claim 1, wherein the inert substance is porcelain Raschig rings.

13. The method of claim 1, wherein a second pressure drop of the reaction tubes, measured after 1 year of acrolein production, relative to a first pressure drop measured prior to the acrolein production, is less than in an otherwise identical method employing an inert substance having a major-axis length less than 1.7 times a major-axis length of the catalyst.

14. The method of claim 1, wherein a second pressure drop of the reaction tubes, measured after 1 year of acrolein production, relative to a first pressure drop measured prior to the acrolein production, is less than in an otherwise identical method employing an inert substance having a major-axis length no more than 1.6 times a major-axis length of the catalyst.

15. The method of claim 1, wherein the catalyst has formula (I)

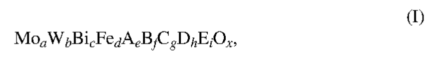

$$Mo_aW_bBi_cFe_dA_eB_fC_gD_hE_iO_x, \quad (I)$$

wherein

A is nickel and/or cobalt,

B is sodium, potassium, rubidium, cesium, and/or thallium,

C is at least one alkaline-earth metal,

D is phosphorus, tellurium, antimony, tin, cerium, lead, niobium, manganese, arsenic, boron, and/or zinc, E is silicon, aluminum, titanium, and/or zirconium, and a, b, c, d, e, f, g, h, i, and x are atomic ratios of Mo, W, Bi, Fe, A, B, C, D, E, and O, and wherein, relative to a being 12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$, $0 \leq i \leq 30$, and x is a value determined according to oxidation states of the Mo, W, Bi, Fe, A, B, C, D, and E elements in the catalyst.

16. The method of claim 15, wherein, in formula (I), relative to a being 12, $$0 \leq b \leq 10,$$

-continued $$0.1 \leq c \leq 10,$$

$$0.1 \leq d \leq 10,$$

$$2 \leq e \leq 15,$$

$$0.001 \leq f \leq 10,$$

$$0 \leq g \leq 10,$$

$$0 \leq h \leq 4, \text{ and}$$

$$0 \leq i \leq 30.$$

17. The method of claim 1, wherein the catalyst has a major-axis length in a range of from 5.0 to 7.0 mm, and wherein the inert substance has a spherical shape, a solid-cylindrical shape, a hollow-cylindrical shape, a saddle shape, and/or a ring shape.

18. The method of claim 1, wherein the catalyst has a major-axis length in a range of from 5.0 to 7.0 mm, and wherein the catalyst has a spherical shape, a solid-cylindrical shape, a hollow-cylindrical shape, a star shape, and/or a ring shape.

19. The method of claim 1, wherein the catalyst has a major-axis length in a range of from 5.0 to 7.0 mm, wherein the catalyst has a spherical shape, a solid-cylindrical shape, a hollow-cylindrical shape, a star shape, and/or a ring shape, and wherein the inert substance has a spherical shape, a solid-cylindrical shape, a hollow-cylindrical shape, a saddle shape, and/or a ring shape.

20. A method for producing (meth) acrolein, the method comprising:

oxidizing propylene or isobutylene by vapor-phase catalytic oxidation in a multitubular reactor comprising a plurality of reaction tubes, the reaction tubes each comprising (i) a reaction zone filled with a catalyst having a formula:

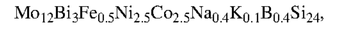

$$Mo_{12}Bi_3Fe_{0.5}Ni_{2.5}Co_{2.5}Na_{0.4}K_{0.1}B_{0.4}Si_{24},$$

and (ii) a cooling zone comprising an inert substance, wherein the catalyst has a spherical shape, a solid-cylindrical shape, a hollow-cylindrical shape, a star shape, and/or a ring shape, wherein a temperature of a heat medium that flows outside the cooling zone is lower than a temperature of a heat medium that flows outside the reaction zone, and wherein the inert substance has a major-axis length that is equal to or more than 1.7times and equal to or less than 3.4 times a major-axis length of the catalyst, and wherein the substance has a thermal conductivity satisfying formula (1):

$$K_{IS} \leq K_{MO_x} \times 0.1, \quad (1)$$

wherein $K_{IS}$ is the thermal conductivity of the inert substance, and $K_{MOx}$ is the thermal conductivity of molybdenum oxide.

* * * * *